(12) United States Patent
Leadbitter

(10) Patent No.: US 6,790,851 B2
(45) Date of Patent: Sep. 14, 2004

(54) FUNGICIDAL COMPOSITIONS

(75) Inventor: Neil Leadbitter, Berkshire (GB)

(73) Assignee: Syngenta Crop Protection, Inc., Greensboro, NC (US)

(*) Notice: Subject to any disclaimer, the term of this patent is extended or adjusted under 35 U.S.C. 154(b) by 1 day.

(21) Appl. No.: 10/258,513

(22) PCT Filed: Apr. 24, 2001

(86) PCT No.: PCT/EP01/04624
§ 371 (c)(1),
(2), (4) Date: Mar. 11, 2003

(87) PCT Pub. No.: WO01/80643
PCT Pub. Date: Nov. 1, 2001

(65) Prior Publication Data
US 2003/0166669 A1 Sep. 4, 2003

(30) Foreign Application Priority Data
Apr. 26, 2000 (GB) .............................. 0010198

(51) Int. Cl.⁷ ................... A01N 43/54; A61K 31/505
(52) U.S. Cl. .................................................. 514/269
(58) Field of Search .......................... 514/269; 504/136

(56) References Cited
FOREIGN PATENT DOCUMENTS

| EP | 0897904 | | 2/1999 |
|---|---|---|---|
| EP | 899255 | * | 3/1999 |
| EP | 0899255 | | 3/1999 |
| EP | 0933025 | | 8/1999 |
| EP | 1023834 | * | 8/2000 |
| WO | 0076317 | | 12/2000 |

* cited by examiner

Primary Examiner—Alton N. Pryor
(74) Attorney, Agent, or Firm—Rose M. Allen

(57) ABSTRACT

The invention comprises a method of combating phytopathogenic diseases on crop plants which comprises applying to the crop plants or the locus thereof being infested with said phytopathogenic disease an effective amount of a combination of
a) a benzophenone of formula I

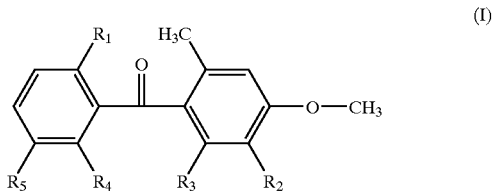

wherein $R_1$ is methoxy, methyl, hydroxy, acetoxy or pivaloyloxy,
$R_2$ is $C_1$–$C_4$alkoxy or 2-halogenbenzyloxy,
$R_3$ is $C_1$–$C_4$alkoxy,
$R_4$ is $C_1$–$C_4$alkyl, halogen or trifluoromethyl, and
$R_5$ is hydrogen, halogen, $C_1$–$C_4$alkoxy, trifluoromethyl or nitro; in association with
b) the strobilurin of formula II

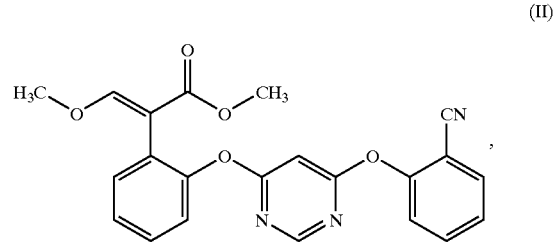

and a composition comprising fungicidally effective amounts of components I and II and a composition.

5 Claims, No Drawings

FUNGICIDAL COMPOSITIONS

The present invention relates to novel fungicidal compositions for the treatment of phytopathogenic diseases of crop plants, especially phytopathogenic fungi, and to a method of combating phytopathogenic diseases on crop plants.

It is known that certain substituted benzophenone derivatives have biological activity with high systemicity against phytopathogenic fungi, e.g. known from EP-A-897904, EP-A-899255 and EP-A-967196 where their properties and methods of preparation are described. On the other hand certain strobilurin derivatives, cyanoimidazole and carbonic acid amide compounds are known from the literature as plant fungicides for application in various crops of cultivated plants. However, crop tolerance and activity against phytopathogenic plant fungi of the known compounds do not always satisfy the needs of agricultural practice in many incidents and aspects.

It has now been found that the use of
a) a benzophenone of formula I

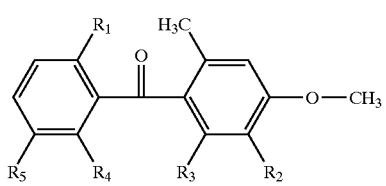

(I)

wherein
R$_1$ is methoxy, methyl, hydroxy, acetoxy or pivaloyloxy,
R$_2$ is C$_1$–C$_4$alkoxy or 2-halogenbenzyloxy,
R$_3$ is C$_1$–C$_4$alkoxy,
R$_4$ is C$_1$–C$_4$alkyl, halogen or trifluoromethyl, and
R$_5$ is hydrogen, halogen, C$_1$–C$_4$alkoxy, trifluoromethyl or nitro; in association with
b) the strobilurin of formula II

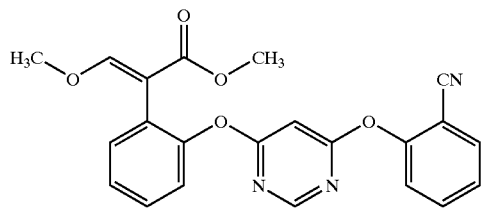

(II)

is particularly effective in combating or preventing fungal diseases of crop plants. These combinations exhibit synergistic fungicidal activity.

The compounds of formula I are known from EP-A-897904, EP-A-899255 and EP-A-967196. Specific examples of preferred individual compounds are listed in the following table.

| No. | R$_1$ | R$_2$ | R$_3$ | R$_4$ | R$_5$ |
|---|---|---|---|---|---|
| 1.01 | OCH$_3$ | OCH$_3$ | OCH$_3$ | CH$_3$ | Br |
| 1.02 | OCH$_3$ | OCH$_3$ | OCH$_3$ | CH$_3$ | Cl |
| 1.03 | OCH$_3$ | OC$_2$H$_5$ | OCH$_3$ | CH$_3$ | Cl |
| 1.04 | OCH$_3$ | OC$_3$H$_7$-n | OCH$_3$ | CH$_3$ | Cl |

-continued

| No. | R$_1$ | R$_2$ | R$_3$ | R$_4$ | R$_5$ |
|---|---|---|---|---|---|
| 1.05 | OCH$_3$ | OCH$_3$ | OCH$_3$ | CH$_3$ | CF$_3$ |
| 1.06 | OCH$_3$ | OCH$_3$ | OCH$_3$ | Cl | H |
| 1.07 | OCH$_3$ | OCH$_3$ | OCH$_3$ | CF$_3$ | H |
| 1.08 | OCH$_3$ | OCH$_3$ | OCH$_3$ | CH$_3$ | H |
| 1.09 | OCH$_3$ | OCH$_3$ | OCH$_3$ | Cl | Br |
| 1.10 | OCH$_3$ | OCH$_3$ | OCH$_3$ | Cl | CH$_3$ |
| 1.11 | CH$_3$ | OCH$_3$ | OCH$_3$ | CH$_3$ | Cl |
| 1.12 | CH$_3$ | OCH$_3$ | OCH$_3$ | CH$_3$ | Br |
| 1.13 | CH$_3$ | OCH$_3$ | OCH$_3$ | CH$_3$ | NO$_2$ |
| 1.14 | CH$_3$ | OCH$_3$ | OCH$_3$ | CH$_3$ | OCH$_3$ |
| 1.15 | CH$_3$ | OCH$_3$ | OC$_4$H$_9$-n | CH$_3$ | Cl |
| 1.16 | CH$_3$ | OCH$_3$ | OC$_4$H$_9$-n | CH$_3$ | Br |
| 1.17 | CH$_3$ | OCH$_3$ | OC$_4$H$_9$-n | CH$_3$ | NO$_2$ |
| 1.18 | CH$_3$ | OCH$_3$ | OC$_4$H$_9$-n | CH$_3$ | OCH$_3$ |
| 1.19 | CH$_3$ | —OCH$_2$-2-F—C$_6$H$_4$ | OC$_4$H$_9$-n | CH$_3$ | Cl |
| 1.20 | CH$_3$ | —OCH$_2$-2-F—C$_6$H$_4$ | OC$_4$H$_9$-n | CH$_3$ | Br |
| 1.21 | CH$_3$ | —OCH$_2$-2-F—C$_6$H$_4$ | OC$_4$H$_9$-n | CH$_3$ | NO$_2$ |
| 1.22 | CH$_3$ | —OCH$_2$-2-F—C$_6$H$_4$ | OC$_4$H$_9$-n | CH$_3$ | OCH$_3$ |
| 1.23 | OH | | OCH$_3$ | CH$_3$ | H |
| 1.24 | CH$_3$—CO—O— | OCH$_3$ | OCH$_3$ | CH$_3$ | H |
| 1.25 | OH | | OCH$_3$ | CH$_3$ | Br |
| 1.26 | CH$_3$—CO—O— | OCH$_3$ | OCH$_3$ | CH$_3$ | Br |
| 1.27 | OH | | OCH$_3$ | CH$_3$ | Cl |
| 1.28 | CH$_3$—CO—O— | OCH$_3$ | OCH$_3$ | CH$_3$ | Cl |
| 1.29 | (CH$_3$)$_3$C—CO—O— | OCH$_3$ | OCH$_3$ | CH$_3$ | Br |

The chemical designation of the above listed compounds is as follows:

1.01 5-bromo-6,6'-dimethyl-2,2',3',4'-tetramethoxy-benzophenone,
1.02 5-chloro-6,6'-dimethyl-2,2',3',4'-tetramethoxy-benzophenone,
1.03 5-chloro-6,6'-dimethyl-3'-ethoxy-2,2',4'-trimethoxy-benzophenone,
1.04 5-chloro-6,6'-dimethyl-3'-propoxy-2,2',4'-trimethoxy-benzophenone,
1.05 5-trifluoromethyl-6,6'-dimethyl-2,2',3',4'-tetramethoxy-benzophenone,
1.06 6-chloro-6'-methyl-2,2',3',4'-tetramethoxy-benzophenone,
1.07 6-trifluoromethyl-6'-methyl-2,2',3',4'-tetramethoxy-benzophenone,
1.08 6,6'-dimethyl-2,2',3',4'-tetramethoxy-benzophenone,
1.09 5-bromo-6-chloro-6'-methyl-2,2',3',4'-tetramethoxy-benzophenone,
1.10 6-chloro-5,6'-dimethyl-2,2',3',4'-tetramethoxy-benzophenone,
1.11 5-chloro-2,6,6'-trimethyl-2',3',4'-trimethoxy-benzophenone,
1.12 5-bromo-2,6,6'-trimethyl-2',3',4'-trimethoxy-benzophenone,
1.13 5-nitro-2,6,6'-trimethyl-2',3',4'-trimethoxy-benzophenone,
1.14 2,6,6'-trimethyl-5,2',3',4'-tetramethoxy-benzophenone,
1.15 5-chloro-2,6,6'-trimethyl-2'-butoxy-3',4'-dimethoxy-benzophenone,
1.16 5-bromo-2,6,6'-trimethyl-2'-butoxy-3',4'-dimethoxy-benzophenone,
1.17 5-nitro-2,6,6'-trimethyl-2'-butoxy-3',4'-dimethoxy-benzophenone,
1.18 2,6,6'-trimethyl-2'-butoxy-5,3',4'-trimethoxy-benzophenone,
1.19 5-chloro-2,6,6'-trimethyl-2'-(o-fluorobenzyloxy)-3',4'-dimethoxy-benzophenone, 1.20 5-bromo-2,6,6'-trimethyl-2'-(o-fluorobenzyloxy)-3',4'-dimethoxy-benzophenone, 1.21 5-nitro-2,6,6'-trimethyl-2'-(o-fluorobenzyloxy)-3',4'-dimethoxy-benzophenone, 1.22 2,6,6'-trimethyl-2'-(o-fluorobenzyloxy)-5,3',4'-trimethoxy-benzophenone, 1.23 6,6'-dimethyl-2-hydroxy-2',3',4'-trimethoxy-benzophenone, 1.24 6,6'-dimethyl-2-acetoxy-2',3',4'-trimethoxy-benzophenone, 1.25 5-bromo-6,6'-dimethyl-2-hydroxy-2',3',4'-trimethoxy-benzophenone, 1.26 5-bromo-6,6'-dimethyl-2-acetoxy-2',3',4'-trimethoxy-benzophenone, 1.27 5-chloro-6,6'-dimethyl-2-hydroxy-2',3',4'-trimethoxy-benzophenone, 1.28 5-chloro-6,6'-dimethyl-2-acetoxy-2',3',4'-trimethoxy-benzophenone, and 1.29 5-bromo-6,6'-dimethyl-2-pivaloyloxy-2',3',4'-trimethoxy-benzophenone.

The compound of formula II is known from the literature under common name azoxystrobin, code ICIA5504, e.g. from EP-A-382375.

Among these mixtures those are preferred in which the compound of formula I is one of the compounds 1.01, 1.06, 1.07, 1.08, 1.09, 1.10, 1.11, 1.12, 1.13, 1.14, 1.25, 1.26 or 1.27.

Throughout this document the expression combination stands for the various combinations of components a) and b), e.g. in a single "ready-mix" form, in a combined spray mixture composed from separate formulations of the single active ingredient components, e.g. a "tank-mix", and in a combined use of the single active ingredients when applied in a sequential manner, i.e. one after the other with a reasonably short period, e.g. a few hours or days. The order of applying the components a) and b) is not essential for working the present invention.

The combinations according to the invention may also comprise more than one of the active components a), if broadening of the spectrum of disease control is desired. For instance, it may be advantageous in the agricultural practice to combine two or three components a) with the compound of formula II.

The active ingredient combinations are effective against phytopathogenic fungi belonging to the following classes: Ascomycetes (e.g. Venturia, Podosphaera, Erysiphe, Monilinia, Mycosphaerella, Uncinula); Basidiomycetes (e.g. the genus Hemileia, Rhizoctonia, Puccinia); *Fungi imperfecti* (e.g. Botrytis, Helminthosporium, Rhynchosporium, Fusarium, Septoria, Cercospora, Alternaria, Pyricularia and *Pseudocercosporella herpotrichoides*); Oomycetes (e.g. Phytophthora, Peronospora, Bremia, Pythium, Plasmopara).

Target crops for the areas of indication disclosed herein comprise within the scope of this invention e.g. the following species of plants: cereals (wheat, barley, rye, oats, rice, sorghum and related crops); beet (sugar beet and fodder beet); pomes, stone fruit and soft fruit (apples, pears, plums, peaches, almonds, cherries, strawberries, raspberries and black-berries); leguminous plants (beans, lentils, peas, soybeans); oil plants (rape, mustard, poppy, olives, sunflowers, coconut, castor oil plants, cocoa beans, groundnuts); cucumber plants (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); or plants such as maize, tobacco, nuts, coffee, sugar cane, tea, vines, hops, turf, bananas and natural rubber plants, as well as ornamentals (flowers, shrubs, broad-leaved trees and evergreens, such as conifers). This list does not represent any limitation.

The combinations of the present invention may also be used in the area of protecting technical material against attack of fungi. Technical areas include wood, paper, leather, constructions, cooling and heating systems, ventilation and air conditioning systems, and the like. The combinations according the present invention can prevent the disadvantageous effects such as decay, discoloration or mold.

The combinations according to the present invention are particularly effective against powdery mildews and rusts, pyrenophora, rhynchosporium, tapesia, fusarium and leptosphaeria fungi, in particular against pathogens of monocotyledonous plants such as cereals, including wheat and barley. They are furthermore particularly effective against downy mildew species, powdery mildews, leaf spot diseases and rusts in dicotyledonous plants.

The amount of combination of the invention to be applied, will depend on various factors such as the compound employed, the subject of the treatment (plant, soil, seed), the type of treatment (e.g. spraying, dusting, seed dressing), the purpose of the treatment (prophylactic or therapeutic), the type of fungi to be treated and the application time.

It has been found that the use of compounds of formula II in combination with the compound of formula I surprisingly and substantially enhance the effectiveness of the latter against fungi, and vice versa. Additionally, the method of the invention is effective against a wider spectrum of such fungi that can be combated with the active ingredients of this method, when used solely.

The weight ratio of a):b) is so selected as to give a synergistic fungicidal action. In general the weight ratio of a):b) is between 200:1 and 1:40. The synergistic action of the composition is apparent from the fact that the fungicidal action of the composition of a)+b) is greater than the sum of the fungicidal actions of a) and b).

The method of the invention comprises applying to the treated plants or the locus thereof in admixture or separately, a fungicidally effective aggregate amount of a compound of formula I and a compound of component b).

The term locus as used herein is intended to embrace the fields on which the treated crop plants are growing, or where the seeds of cultivated plants are sown, or the place where the seed will be placed into the soil. The term seed is intended to embrace plant propagating material such as cuttings, seedlings, seeds, germinated or soaked seeds.

The novel combinations are extremely effective on a broad spectrum of phytopathogenic fungi. Some of them have a systemic action and can be used as foliar and soil fungicides and for seed dressing.

The fungicidal combinations are of particular interest for controlling a large number of fungi in various crops or their seeds, especially wheat, rye, barley, oats, rice, maize, lawns, cotton, soybeans, coffee, sugarcane, fruit and ornamentals in horticulture and viticulture, in vegetables such as cucumbers, beans and cucurbits, and in field crops such as potatoes, peanuts, tobacco and sugarbeets.

The combinations are applied by treating the fungi or the seeds, plants or materials threatened by fungus attack, or the soil with a fungicidally effective amount of the active ingredients.

The agents may be applied before or after infection of the materials, plants or seeds by the fungi.

The novel combinations are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
Rhizoctonia species in cotton, potatoes, rice and lawns,
Ustilago species in cereals and sugarcane,
*Venturia inaequalis* (scab) in apples,
Helminthosporium species in cereals,
*Septoria nodorum* in wheat,
*Septoria tritici* in wheat,
*Rhynchosporium secalis* on barley,
*Botrytis cinerea* (gray mold) in strawberries, tomatoes and grapes,
*Cercospora arachidicola* in groundnuts,
*Peronospora tabacina* in tobacco, or other Peronospora in various crops,
*Pseudocercosporella herpotrichoides* in wheat and barley,
*Pyrenophera teres* in barley,
*Pyricularia oryzae* in rice,
*Phytophthora infestans* in potatoes and tomatoes,
Fusarium and Verticillium species in various plants,
*Plasmopara viticola* in grapes,
Alternaria species in fruit and vegetables,
*Pseudoperonospora cubensis* in cucumbers,
*Mycosphaerella fijiensis* in banana,
Colleotrichum species in various crops.

When applied to the plants the compounds of formula I are applied at a rate of 20 to 2000 g/ha, particularly 20 to 1000 g/ha, e.g. 20, 30, 40, 75, 80, 100, 125, 150, 175, 200, 300, 500, 750, 1000, 1200, 1500 or 2000 g/ha, in association with 10 to 750 g/ha, particularly 20 to 1000 g/ha, e.g. 12.5 g/ha, 15 g/ha, 30 g/ha, 40 g/ha, 60 g/ha, 75 g/ha, 80/ha, 100 g/ha, 125 g/ha, 150 g/ha, 175 g/ha, 200 g/ha, 250 g/ha, 300 g/ha, 500 g/ha, 600 g/ha or 750 g/ha of the compound of formula II.

In agricultural practice the application rates of the combination depend on the type of effect desired, and range from 0.02 to 3 kg of active ingredient per hectare.

When the active ingredients are used for treating seed, rates of 0.001 to 50 g a.i. per kg, and preferably from 0.01 to 10 g per kg of seed are generally sufficient.

The invention also provides fungicidal compositions comprising a compound of formula I and the compound of formula II.

The composition of the invention may be employed in any conventional form, for example in the form of a twin pack, an instant granulate, a flowable formulation, an emulsion concentrate or a wettable powder in combination with agriculturally acceptable adjuvants. Such compositions may be produced in conventional manner, e.g. by mixing the active ingredients with appropriate adjuvants (diluents or solvents and optionally other formulating ingredients such as surfactants). Also conventional slow release formulations may be employed where long lasting efficacy is intended.

Particularly formulations to be applied in spraying forms such as water dispersible concentrates or wettable powders may contain surfactants such as wetting and dispersing agents, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% agriculturally acceptable surfactant and 10 to 99.99% solid or liquid adjuvant(s), the active agent consisting of at least a compound of formula I together with the compound of formula II, and optionally other active agents, particularly microbides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ dilute formulations.

The Examples which follow serve to illustrate the invention, "active ingredient" denoting a mixture of compound I and a compound of component b) in a specific mixing ratio.

| Formulation Examples | | | |
|---|---|---|---|
| Wettable powders | a) | b) | c) |
| active ingredient [comp a:comp b] = 1:3(a), 1:2(b), 1:1(c)] | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7–8 mol of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| Emulsifiable concentrate | |
|---|---|
| active ingredient (comp a:comp b) = 1:6) | 10% |
| octylphenol polyethylene glycol ether (4–5 mol of ethylene oxide) | 3% |
| calcium dodecylbenzenesulfonate | 3% |
| castor oil polyglycol ether (35 mol of ethylene oxide) | 4% |
| cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| active ingredient [comp a:comp b) = 1:6(a), 1:2(b), 1:10(c)] | 5% | 6% | 4% |

-continued

| Dusts | a) | b) | c) |
|---|---|---|---|
| talcum | 95% | — | — |
| kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

| Extruder granules | |
|---|---|
| active ingredient (comp a:comp b) = 2:1) | 15% |
| sodium lignosulfonate | 2% |
| carboxymethylcellulose | 1% |
| kaolin | 82% |

The active ingredient is mixed and ground with the adjuvants, and the mixture is moistened with water. The mixture is extruded and then dried in a stream of air.

| Coated granules | |
|---|---|
| active ingredient (comp a:comp b) = 1:10) | 8% |
| polyethylene glycol (mol. wt. 200) | 3% |
| kaolin | 89% |

The finely ground active ingredient is uniformly applied, in a mixer, to the kaolin moistened with polyethylene glycol. Non-dusty coated granules are obtained in this manner.

| Suspension concentrate | |
|---|---|
| active ingredient (comp a:comp b) = 1:8) | 40% |
| propylene glycol | 10% |
| nonylphenol polyethylene glycol ether (15 mol of ethylene oxide) | 6% |
| sodium lignosulfonate | 10% |
| carboxymethylcellulose | 1% |
| silicone oil (in the form of a 75% emulsion in water) | 1% |
| water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of a combination of the compound of formula I (component a) and a compound of component b), or of each of these compounds separately, are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed.

The obtained capsule suspension is stabilized by adding 0.25 parts of a thickener and 3 parts of a dispersing agent. The capsule suspension formulation contains 28% of the active ingredients. The medium capsule diameter is 8–15 microns.

The resulting formulation is applied to seeds as an aqueous suspension in an apparatus suitable for that purpose.

BIOLOGICAL EXAMPLES

A synergistic effect exists whenever the action of an active ingredient combination is greater than the sum of the actions of the individual components.

The action to be expected E for a given active ingredient combination obeys the so-called COLBY formula and can be calculated as follows (COLBY, S. R. "Calculating synergistic and antagonistic responses of herbicide combinations". Weeds, Vol. 15, pages 20–22; 1967):

ppm=milligrams of active ingredient (=a.i.) per liter of spray mixture

X=% action by active ingredient I using p ppm of active ingredient

Y=% action by active ingredient II using q ppm of active ingredient.

According to COLBY, the expected (additive) action of active ingredients I+II using p+q ppm of active ingredient is $$E = X + Y - \frac{X \cdot Y}{100}$$

If the action actually observed (O) is greater than the expected action (E), then the action of the combination is superadditive, i.e. there is a synergistic effect.

Alternatively the synergistic action may also be determined from the dose response curves according to the so-called WADLEY method. With this method the efficacy of the a.i. is determined by comparing the degree of fungal attack on treated plants with that on untreated, similarly inoculated and incubated check plants. Each a.i. is tested at 4 to 5 concentrations. The dose response curves are used to establish the EC90 (i.e. concentration of a.i. providing 90% disease control) of the single compounds as well as of the combinations (EC $90_{observed}$). The thus experimentally found values of the mixtures at a given weight ratio are compared with the values that would have been found were only a complementary efficacy of the components was present (EC 90 $(A+B)_{expected}$). The EC 90 $(A+B)_{expected}$ is calculated according to Wadley (Levi et al., EPPO-Bulletin 16, 1986, 651–657):

$$EC\ 90(A+B)_{expected} = \frac{a+b}{\frac{a}{EC90(A)_{observed}} + \frac{b}{EC90(B)_{observed}}}$$

wherein a and b are the weight ratios of the compounds A and B in the mixture and the indexes (A), (B), (A+B) refer to the observed EC 90 values of the compounds A, B or the given combination A+B thereof. The ratio EC90 $(A+B)_{expected}$/EC90 $(A+B)_{observed}$ expresses the factor of interaction (F). In case of synergism, F is >1.

Example B-1

Efficacy against *Erysiphe graminis* f.sp. *tritici* on Wheat a) Protective Treatment Fifteen wheat seeds c.v. "Arina" are sown in plastic pots of 50 ml and grown for 7 to 12 days at 22/19° C., 50–70% rH in the greenhouse. When the primary leaves have fully expanded, the plants are spray treated with aqueous spray liquids containing the single compounds, or mixtures thereof (hereinafter a.i.). All compounds are used as experimental or commercially available formulations, combinations are applied as tank mixtures. The application comprises foliar spraying to near runoff (three pots per treatment). 7 days after the application, the plants are inoculated in a settling tower with fresh spores of *Erysiphe graminis* f.sp. *tritici* by dusting the conidia on the test plants The plants are then incubated in a growth chamber at 20° C., 60% rH. Six days after inoculation, the percentage of infection on primary leaves is evaluated. The efficacy of the a.i. is determined by comparing the degree of fungal attack on treated plants with that on untreated, similarly inoculated and incubated check plants. Each a.i. is tested at 3 to 5 concentrations. The results are evaluated according to the COLBY method.

b) Curative Treatment

Wheat plants cv. Arina are grown in standard soil in 50 ml pots (approx. 15 plants per pot) in the greenhouse at 22/19° C. and 14 hours light per day. At test begin the plants are 8 days old. For inoculation, conidia are dusted over the test plants and the plants are incubated at 18–20° C. until treatment. The fungicide treatment is carried out 3 days after inoculation by spraying the test plants with diluted spray suspensions of the individual active ingredients or mixtures, being prepared by suspension in demineralized water and appropriate dilution. 12 plants in 3 pots are used for each treatment. 3 to 4 days after treatment the tests are evaluated by estimating the percentage of fungal attack on the leaves. The activity is calculated relative to the disease on the check plants. The fungicide interactions in the mixtures are calculated according to the COLBY method.

Example B-2

Activity against *Uncinula Necator*

Grape plants in the 4–6 leaf stage, variety Gutedel, are inoculated with conidia of *Uncinula necator* by dusting the conidia over the test plants. After 2 days under high humidity and reduced light intensity, the plants are incubated for 10–14 days in a growth chamber at 70% rH and 22° C. 3 days after inoculation the active ingredients and the mixtures are applied by spraying aqueous suspensions being prepared by suspending the a.i.s in demineralized water and appropriate dilution. 5 plants are used for every treatment. 12 days after inoculation the tests are evaluated by estimating the percentage of fungal leaf attack relative to the disease on the check plants. The fungicide interactions in the mixtures are calculated according to COLBY method.

The mixtures according to the invention exhibit good activity in the methods of the above Biological Examples 1 and 2.

What is claimed is:

1. A method of combating phytopathogenic diseases on crop plants which comprises applying to the crop plants or the locus thereof being infested with said phytopathogenic disease an effective amount of a combination of a) a benzophenone of formula I

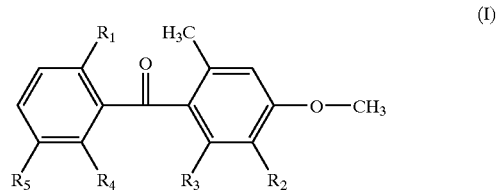

wherein $R_1$ is methoxy, hydroxy, acetoxy or pivaloyloxy, $R_2$ is $C_1$–$C_4$alkoxy or 2-halogenbenzyloxy, $R_3$ is $C_1$–$C_4$alkoxy, $R_4$ is $C_1$–$C_4$alkyl, halogen or trifluoromethyl, and $R_5$ is hydrogen, halogen, $C_1$–$C_4$alkoxy, trifluoromethyl or nitro; and b) the strobilurin of formula II

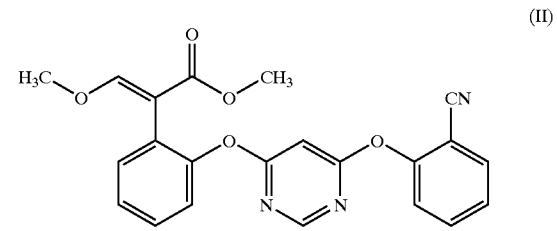

; and wherein in the weight ratio of a) to b) is between 200:1 and 1:40.

2. A method according to claim 1 wherein the applied amounts of the components a) and b) are so selected as to enhance the fungicidal activity of each other in a synergistic manner.

3. A method according to claim 1 wherein component a) is selected from the group comprising 5-bromo-6,6'-dimethyl-2,2',3',4'-tetramethoxy-benzophenone, 6-chloro-6'- ethyl-2,2',3',4'-tetramethoxy-benzophenone, 6-trifluoromethyl-6'-methyl-2,2',3',4'-tetramethoxy-benzophenone, 6,6'-dimethyl-2,2',3',4'-tetramethoxy-benzophenone, 5-bromo-6-chloro-6'-methyl-2,2',3', 4'-tetramethoxy-benzophenone, 6-chloro-5,6'-dimethyl-2,2',3',4'-tetramethoxy-benzophenone, 5-bromo-6,6'-dimethyl-2-hydroxy-2',3', 4'-trimethoxy-benzophenone, 5-bromo-6,6'-dimethyl-2-acetoxy-2',3',4'-trimethoxy-benzophenone, and 5-chloro-6,6'-dimethyl-2-hydroxy-2',3',4'-trimethoxy-benzophenone.

4. A fungicidal composition comprising a fungicidally effective combinatic of components a) and b) wherein a) is a benzophenone of formula I

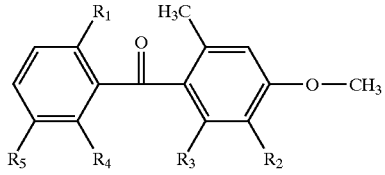

wherein

R₁ is methoxy, hydroxy, acetoxy or pivaloyloxy,

R₂ is $C_1$–$C_4$alkoxy or 2-halogenbenzyloxy,

R₃ is $C_1$–$C_4$alkoxy,

R₄ is $C_1$–$C_4$alkyl, halogen or trifluoromethyl, and R₅ is hydrogen, halogen, $C_1$–$C_4$alkoxy, trifluoromethyl or nitro; and b) is the strobilurin of formula II

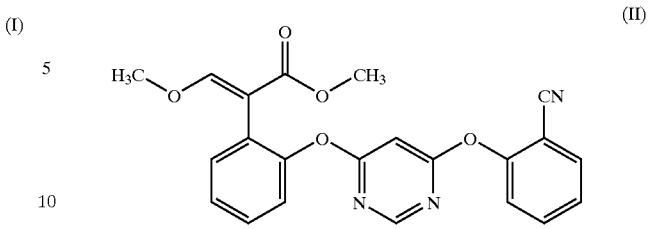

together with an agriculturally acceptable carrier, and optionally a surfactant

; and wherein in the weight ratio of a) to b) is between 200:1 and 1:40.

5. A composition according to claim 4 wherein the ratio of components a) and b) are so selected that the fungicidal activity is synergistically enhanced.

\* \* \* \* \*